US007972623B2

(12) United States Patent
Gergely et al.

(10) Patent No.: US 7,972,623 B2
(45) Date of Patent: Jul. 5, 2011

(54) METHOD FOR THE PRODUCTION OF EFFERVESCENT GRANULES IN A VACUUM

(75) Inventors: Irmgard Gergely, Vienna (AT); Thomas Gergely, Vienna (AT); Stefan Gergely, Vienna (AT)

(73) Assignee: Dr. Gergely & Co., Vienna (AT)

( * ) Notice: Subject to any disclaimer, the term of this patent is extended or adjusted under 35 U.S.C. 154(b) by 880 days.

(21) Appl. No.: 10/568,712

(22) PCT Filed: Aug. 7, 2004

(86) PCT No.: PCT/EP2004/008879
§ 371 (c)(1),
(2), (4) Date: Aug. 8, 2007

(87) PCT Pub. No.: WO2005/018602
PCT Pub. Date: Mar. 3, 2005

(65) Prior Publication Data
US 2008/0003289 A1 Jan. 3, 2008

(30) Foreign Application Priority Data
Aug. 20, 2003 (AT) ................................ A 1309/2003

(51) Int. Cl.
*A61K 9/46* (2006.01)
(52) U.S. Cl. ......................... 424/466; 424/489; 514/951
(58) Field of Classification Search ........................ None
See application file for complete search history.

(56) References Cited

U.S. PATENT DOCUMENTS
4,678,661 A    7/1987  Gergely et al.
4,911,930 A *  3/1990  Gergely et al. ............... 424/466

FOREIGN PATENT DOCUMENTS
EP    0037675    10/1981
EP    0076340    4/1983

OTHER PUBLICATIONS
International Search Report (PCT/EP2004/008879) dated Apr. 15, 2005, 5 pages.

* cited by examiner

*Primary Examiner* — Robert A Wax
*Assistant Examiner* — Hasan S Ahmed
(74) *Attorney, Agent, or Firm* — Rothwell, Figg, Ernst & Manbeck, P.C.

(57) ABSTRACT

The invention relates to a method for producing effervescent granules, in which the reaction partners edible, organic acid components and alkaline effervescent components separating carbon dioxide are reacted with each other in a vacuum under the effect of gas in a container that can be evacuated. The container is evacuated to a first vacuum value within a vacuum range of 200-900 mbar, whereupon the pressure inside the container is increased to a second vacuum value as a result of the gases produced during the reaction. The steps are cyclically repeated while the reaction continues. A maximum number of cycles, a maximum reaction time, and optionally, a maximum load for the stirring apparatus are defined before the reaction begins, and the reaction is terminated after reaching the first of the maximums. In an alternative embodiment, the invention also relates to a method for improving the shelf life of effervescent granules by a treatment with carbon dioxide during and/or following the production of the effervescent granules, and effervescent particles treated in this manner.

59 Claims, No Drawings

METHOD FOR THE PRODUCTION OF EFFERVESCENT GRANULES IN A VACUUM

CROSS-REFERENCE TO RELATED APPLICATION

This application is a National Phase of International Application Serial No. PCT/EP2004/008879, filed Aug. 7, 2004.

BACKGROUND OF THE INVENTION

1. Field of the invention

The invention relates to a method for the production of effervescent granules, in which the reactants are reacted in a vacuum in an evacuatable container with evolution of gas.

2. Background of the Invention

Effervescent granules and effervescent tablets can be prepared by mixing of alkaline constituents eliminating carbon dioxide, in particular bicarbonates or carbonates, with preferably edible, organic acids and subsequent direct tabletting, by granulation of the effervescent components in a fluidized-bed drier or granulation and subsequent drying on trays. In the preparation of effervescent granules, however, granulation in a vacuum is becoming increasingly important.

Vacuum granulation is advantageous in the so-called "reactive" granulation for effervescent granules, in which the acids and/or the acidic salts thereof are reacted with the alkaline constituents and are granulated. The reactive constituents react with one another after addition of polar solvents, such as water or mixtures of water with alcohols or binder solutions or as a result of hydration of at least one reactive constituent. However, particular process control measures are required for controlling this reaction.

PCT/US94/02870 describes a method for the granulation of effervescent components, the granules being dried after the reaction in a vacuum. The granulation is effected at atmospheric pressure and with stepwise addition of the liquid, with the result that the reaction can be better controlled. By applying a vacuum and increasing the temperature, the reaction—before the complete conversion of the acid—between the effervescent components is stopped and the excess liquid is removed. However, the information is not specific and gives no indication of the determination of the end product of the reaction by measurement of the evolution of carbon-dioxide.

U.S. Pat. No. 4,824,664 describes a method in which the liquid required for the reaction is aspirated in a vacuum of 600 mbar. The reaction then takes place under atmospheric pressure over a period of from 25 to 40 minutes, whereupon the reaction is stopped by drying in a vacuum. On the one hand, this is much too slow for an efficient production method and, on the other hand, the reaction takes place in an uncontrollable manner in this time span.

U.S. Pat. No. 4,678,661 describes a method in which the reaction is allegedly controlled by measurement of the pressure difference which, however, is insufficient without controlling the time factor. After respective intermediate drying, raw materials are added, and the reaction is started again by adding liquid, which lengthens the production time in an undesired manner.

EP-B1-76 340 describes a granulation method for a pulverulent or granular mixture in a closed system in a vacuum, a pressure above the resulting partial pressure of the solvent and below atmospheric pressure being maintained. The vacuum at the start of the reaction must be as low as possible (from about 10 to 20 mbar). During the vacuum treatment, a metered amount of the solvent is added to the mixture for passivating the surface of at least one of the reaction components. After 1000 mbar has been reached by the evolution of carbon dioxide from the time of addition of the solvent, the mixture is dried. This treatment—addition of solvent and drying—is repeated until the surface passivation indicated by substantial slowing down of the reaction or reduced gas evolution is reached. The amount of carbon dioxide evolved at 1000 mbar serves as a parameter for the degree of passivation of the surface. The course of the reaction between 10 and 1000 mbar can easily lead to an overreaction and undesired considerable granulation owing to the water formed in the reaction and not removed by suction.

In U.S. Pat. No. 4,911,930 a hot air or vapor stream is aspirated into the granules by means of reduced pressure and cannot serve for controlling the reaction.

Disadvantages of the methods mentioned are that the parameters required for carrying out an optimum reaction are neither uniquely reproducible from batch to batch nor definable independently of the influence of the batch-related differences in raw material. The reaction of the effervescent component is also influenced by the water formed during the reaction. Depending on the quality of the raw materials, the reaction can take place more weakly or more vigorously, with the result that different amounts of water form per unit time. Owing to these varying reaction circumstances, the control of the method by the time alone or by the carbon dioxide measurement alone is decisively more difficult or the highly desired possibility of automation is virtually ruled out.

If only the time span (as, for example, according to U.S. Pat. No. 5,312,626 or EP-A1-525,388) in which the reaction takes place is regarded as an essential parameter, this may vary in the case of different raw material qualities, for example in the case of different residual moisture content, particle size, etc. of the acids and/or their acidic salts or the alkali metal constituents eliminating carbon dioxide and can lead to different results, such as to excessive granulation with agglomerate formation, or to insufficient granulation.

It has therefore been found that the methods corresponding to the prior art were not suitable for achieving standardized methods for fully automatic production. In addition—as already mentioned—the intermediate drying and the repetition of the granulation step lengthens the production times to an undesired extent.

SUMMARY OF THE INVENTION

It was an object of the invention to develop a method for the production of effervescent granules which permits a controlled course of the chemical reaction and standardized, reproducible process control and can compensate for deviations of the raw material qualities, for example with regard to a fully automatic computer-controlled course.

According to the invention, the good controllability of the reaction is provided by virtue of the fact that the reaction is carried out in a vacuum range of from 200 to 900 mbar and the evacuation of the container to the first vacuum value is repeated, after gas evolution is complete, to a second vacuum value, optionally repeated several times, and the reaction taking place in cycles without intermediate drying is then stopped by drying the resulting effervescent granules in a vacuum. Furthermore, by the choice of the first and second vacuum parameter and hence of the pressure difference for the gas evolution by the reaction and by the choice of the maximum number of cycles, the maximum duration of the reaction and optionally—as a safety measure—an upper limit of, for example, 160 amps for the current consumption of the stirrer (stirrer load).

Very specific reaction characteristics can thus be created for different effervescent granules depending on ingredients, after the specification of which the further production batches can take place automatically.

Even in the case of differences relating to raw materials and associated deviation of the reaction behavior, an optimum course of the reaction can be achieved by stopping the reaction by drying in a vacuum after reaching one of the specified maxima, i.e. the maximum number of cycles or a maximum duration of reaction.

DETAILED DESCRIPTION OF THE PREFERRED EMBODIMENTS

According to the invention, the reactive constituents are reacted with one another in a vacuum in an evacuatable container, the container being evacuated to a first vacuum value, and the first vacuum value being chosen so that the reaction continues and is not stopped, and the pressure in the container due to the gasses forming during the reaction is then allowed to increase with a specified pressure difference up to a second vacuum value. This step is repeated cyclically by repeated, controlled opening and closing of the valve to the vacuum pump, with a specified number of cycles in a specified time, after which the reaction is stopped by drying in a vacuum. Consequently, the evolution of carbon dioxide and of steam can be slowed down and controlled. The term "pendulum vacuum" was coined for this process.

The characteristic data and parameters of the pendulum vacuum, such as the pressure difference, the first and second vacuum value and the number of cycles and the time span in which the cycles take place, optionally also the maximum of the stirrer load, can be specified. With the specification of these parameters essential for the course of the reaction, independently of different raw material qualities, all further production batches of a product can be run fully automatically and these data can be established in a product-specific manner for each product and can be specified for the further production. This is particularly important for automated computer-controlled operation.

An advantage of the method according to the invention is that water forming in the reaction—depending on the vapor pressure at the chosen vacuum values—or the solvent introduced evaporates in the course of the reactive granulation as a result of the choice of the vacuum range and the chosen pressure difference and as a result of the number of cycles in a predetermined time in the reduced vacuum and thus does not influence the reaction in a secondary process. As a result, specific and readily controllable reactions are permitted and an uncontrollable chain reaction is avoided.

Owing to the slowed down and controlled reaction with a pendulum vacuum, a direct sequence of reaction cycles can take place without intermediate drying, whereupon, after the end of the specified number of cycles, within a predetermined time span, the granules can be dried and can be comminuted to the desired particle size.

In the present Application, "vacuum" is understood as meaning a state of space having a pressure reduced relative to the ambient air. It is important that the pressure increase to the second vacuum value does not take place up to the atmospheric pressure which prevails at the location. The second vacuum value should be at least 10% below the ambient pressure prevailing in each case at the location. The following examples for vacuum values relate to an ambient pressure of 1 bar.

The pressure difference between the first and second vacuum value should be from 200 to 700 mbar, preferably from 300 to 500 mbar, and a controlled reaction should take place cyclically in a vacuum range of from 200 to 900 mbar.

The first vacuum value is chosen so that a portion of the amount of liquid required for starting the reaction remains behind in the reaction container after the first evacuation to the first vacuum value and hence sufficient moisture is present for the continuation of the reaction after reevacuation to the first vacuum value. The pressure increase up to the second vacuum value is established as a function of the reactivity of the reactive constituents and the amount of carbon dioxide and steam forming as a result of the reaction. For precise control of the course of the reaction, the parameters of the method, i.e. the first and the second vacuum value and also the pressure difference, can be varied from cycle to cycle.

The reaction taking place in cycles can also be repeated after the additional introduction of solids or liquids without intermediate drying.

For carrying out the automated method, the evacuatable container, for example a drum or a vessel, is loaded with the starting materials containing the reactive constituents, the amount of liquid required for starting the reaction is added and the program is started, which can run under automatic control, for example according to the predetermined values of the parameters; first vacuum value of 500 mbar, second vacuum value of 800 mbar, pressure difference of 300 mbar, maximum number of cycles of 4 in a maximum duration of reaction of 5 min. The reaction is stopped after the first maximum is reached, i.e. either the number of cycles or the duration of the method. The reaction can be stopped by vacuum drying. Thereafter, the further process steps, for example admixing of further ingredients, further granulation, final drying, comminution, sieving and emptying, are actuated.

It is possible to use various types of vacuum pumps, such as rotary vane, liquid ring or screw rotor pumps, having a nominal suction capacity adapted to the container size, which pumps should be capable of reaching a final pressure of 0.1 mbar and of evacuating the empty container in from 30 sec to two min to 10 mbar.

In the case of a reactive granulation, the method according to the invention can be used independently of the temperature and method by which the reaction is started. The temperature at which the method according to the invention is carried out is not critical. It is possible to work at room temperature (20° C.) or at an elevated product temperature of, for example, from 40 to 80° C. The liquid which serves as granulating liquid can either be applied to one of the reactants, such as the edible organic acids or the alkaline effervescent constituents eliminating carbon dioxide, before the second reactant is added, or can be introduced directly into a mixture of the effervescent components. The introduction of the liquid can be effected, as described in U.S. Pat. No. 4,824,664, by aspiration in a vacuum. If the raw material of one or both reactants has a higher proportion of residual moisture, the cycles take place more rapidly, over reaction or over granulation being prevented according to the method according to the invention, which is not only time-controlled, by the predetermined number of cycles. At relatively low residual moisture content, the cycles take place more slowly, but in this case the required reaction and granulation are nevertheless achieved by the maximum specified duration of the method.

Apart from polar solvents, binder solutions in water, alcohols or mixtures thereof can also be used as liquids for effervescent granules, such as, for example, polyvinylpyrrolidones, polyethylene glycol or hydroxypropylmethylcellulose, sugar solutions or solutions of sugar alcohols or colloids. Furthermore, it is possible to use reactive solutions, such as, for example, solutions of organic acids in water or water/ethanol, or of acidic salts of the edible organic acids or of the alkaline salts thereof.

The reactive constituents in the case of effervescent granules include at least one acidic effervescent component, i.e. a solid, organic acid and/or the salts thereof, and at least one alkaline effervescent component eliminating carbon dioxide. The organic acid is preferably edible. It is also possible to react with one another a plurality of different organic acids and/or salts thereof and/or effervescent components eliminating carbon dioxide. Furthermore, in certain embodiments of the invention, other components, for example magnesium oxide, may be present as reactive constituents.

The method according to the invention is furthermore suitable for the production of effervescent granules, in which the liberation of water from hydrates of the reactive constituents on heating is utilized for the granulation. "Hydrate" is understood as meaning the chemical compounds of organic or inorganic substances with H2O, the H2O not being a constituent of complex compounds. The bound H2O is also designated as water of crystallization or water of hydration.

It is also possible to use for this purpose water-containing organic acids, such as, for example, citric acid monohydrate or water-containing sodium carbonate, which, with increasing temperature, release water which is required for the reactive granulation. This process is known as "difficult to control in order to achieve reproducible results" (Lachman & Lieberman: Pharmaceutical dosage forms, 1980; page 233). By means of the method according to the invention, on the other hand, it is possible to carry out a readily controllable and reproducible process in which a number of up to 100 cycles, optionally even more than 100 cycles, of the pendulum vacuum between two specified vacuum values takes place in a certain time or up to warming-up of the material to a temperature of from 30 to 80° C., with a result that a part of the water (the amount is dependent on the vapor pressure of the water at the chosen temperature and the chosen vacuum value) and a part of the carbon dioxide is extracted by suction in the repeating cycles and the process can no longer be influenced in an uncontrolled manner.

The method according to the invention can be used for the production of a very wide range of effervescent granules and of effervescent tablets which can be produced from these effervescent granules, for example:

granules comprising pharmaceutical active substances which react with the acidic effervescent components or the alkaline effervescent components, granules comprising pharmaceutical active substances which do not react with the effervescent components used but are granulated together with the effervescent base, effervescent base granules which, after granulation, are mixed with pharmaceutical active substances suitable for effervescent tablets and optionally excipients, neutral substances and flavors. The examples of suitable groups of active substances are: analgesics, antipyretics, antihistamines, antiallergic agents, antibiotics, antidiabetic agents, oncolytic agents, expectorants, electrolyte preparations, laxatives, vitamins, phytopharmaceuticals, cardiovascular agents, antidiarrhoeal agents, diuretics and agents for stimulating blood flow.

In a further embodiment it was found that, by an additional increase of the carbon dioxide partial pressure, not related to the reaction, in the reaction container, at least a part of the residual moisture still adhering to the effervescent crystals after vacuum drying can be "deactivated" and the effervescent system thus made more stable during storage. Usually, the residual moisture content is in the range of from 0.01 to 1% by weight, in particular in the range of from about 0.1 to 0.8% by weight, depending on the effervescent system.

In the case of particularly reactive systems, the additional introduction of carbon dioxide proved to be advantageous for making the process of the reactive granulation even better controllable. Surprisingly, it was found that this simultaneously led to stabilization of the granules in the context of reduced sensitivity to the remaining residual moisture, which could be checked using our own special measuring instruments, on the basis of the liberation of carbon dioxide from the prepared product. This discovery is utilized in a further embodiment of the method according to the invention by the additional introduction of carbon dioxide in the pendulum process and/or during the subsequent final drying.

The advantageous effect mentioned is achieved by allowing additional carbon dioxide gas to flow from an external source into the reaction container with stirring after application of a vacuum in the course of the reaction granulation of effervescent systems, such as, for example, in the cyclic reaction granulation according to the invention under a pendulum vacuum, but especially in the course of the final drying of effervescent systems produced in this manner. In this way, in the reaction granulation, in the course of the cycle and in the final drying of the systems, the increased carbon dioxide partial pressure can lead to a further reduction of the reaction so that—owing to the inflowing carbon dioxide during the reaction granulation—the number of cycles should be typically increased and optionally up to ten times more cycles should take place than in the case of a reaction procedure without external feeding of carbon dioxide.

By means of our own measuring instruments especially developed for this purpose, with the aid of which the tiniest amounts of gas of the order of magnitude of microliters can be exactly measured and documented, it is possible to analyze effervescent systems, regardless of the method of their production, for their reactivity by the residual moisture. On the basis of such measurements it can be shown that the use of the additional increase in carbon dioxide partial pressure actually leads to a significantly improved stability of the effervescent systems.

In a further embodiment, the carbon dioxide partial pressure prevailing in the container is increased—either additionally or for the first time—after the end of the reaction granulation by repeated implosion of carbon dioxide gas into the reaction container. By means of this measure, it is possible to surround or to saturate the effervescent particles with carbon dioxide to such an extent that, even on prolonged storage of the effervescent granules, a carbon dioxide microatmosphere is evidently retained and effectively inhibits or suppresses further reaction of the acidic and alkaline components with one another.

It is known that numerous pharmaceutical active substances, such as, for example, acetylsalicylic acid or acetylcysteine, are very sensitive to residual moisture content in effervescent formulations because, for example, in the case of acetylsalicylic acid, free acetic acid forms through hydrolysis and in turn can initiate a secondary chain reaction. However, it is precisely such a chain reaction that can be substantially reduced owing to the stability-improving measure according to the invention through increasing the carbon dioxide partial pressure. It is a further advantage of this measure that it is applicable not only to a specific method of effervescent production, such as, for example, the reaction granulation by the pendulum vacuum method according to the invention, but very generally to any desired particulate effervescent systems, such as effervescent powders and effervescent granules, regardless of the method of their production.

The invention is explained further by the following examples.

Example 1

Reactive Granulation without Addition of Granulating Liquid

Anhydrous sodium bicarbonate and citric acid monohydrate are loaded into a heatable vacuum granulator in a ratio corresponding to the desired pH and are mixed for 5 min until homogeneity is achieved.

As the temperature increases, the reaction is started by the water liberated from the citric acid monohydrate. For the reaction, a pendulum vacuum with two preselected vacuum values, e.g. 550 and 900 mbar, is chosen, evacuation being effected to 550 mbar and the valve to the vacuum pump being closed. The reaction results in a pressure increase to 900 mbar. At this value, the valve is opened again, the vessel is evacuated again to 550 mbar and this process is repeated several times. After a duration of reaction of from 20 to 40 min or after a temperature of from 40 to 60° C. has been reached, the pendulum vacuum is cut off and the granules are vacuum-dried with full pump power.

Example 2

Reactive Granulation with Addition of Granulating Liquid (Water)

Production of effervescent granules which can be used for a very wide range of pharmaceutical active substances and/or active substance combinations, inter alia vitamins and trace elements, the effervescent granules comminuted to the desired particle size being mixed with the appropriate active substances and sweeteners and optionally flavors and fillers. The granules either can be filled into sachets or, if required, lubricants can be added and said granules can be pressed to give tablets.

A vacuum granulator having a heatable jacket is loaded with 31.78 parts by weight of citric acid, which is heated to 50° C. with stirring. On reaching the temperature, 0.16 parts by weight of water is added with stirring and distributed for 5 min. Thereafter, 12.3 parts by weight of sodium bicarbonate are added, the stirrer and the pendulum vacuum for controlling the reaction are switched on at the predetermined first vacuum value=450 mbar, second vacuum value=850 mbar and the number of 4 cycles (pendulum) within 4 min at the most.

After the end of the fourth cycle (pendulum), e.g. after 3½ min, but no later than after the elapse of 4 min and independently of whether 4 cycles were actually achieved in this time, the program is switched off and full vacuum is applied for drying the granules. The dried granules are sieved to the desired particle size and can, if required, be used as effervescent based granules.

For fully automatic operation, the characteristic data determined for the product, i.e. vacuum range, first and second vacuum value, pressure difference, number of cycles and duration of the pendulum vacuum, can be set, with the result that the method can take place stepwise after respectively reaching the set values.

Example 3

Effervescent Magnesium Granules

The following are introduced into a vacuum granulator having a heatable jacket: 31.4 parts by weight of citric acid, 5.9 parts by weight of magnesium carbonate and optionally sweeteners. Heating to 50° C. is effected with stirring. Thereafter, 0.9 parts by weight of water is added with stirring and the program is switched on. The reaction takes place with a pendulum vacuum at the predetermined values between 500 and 900 mbar and with 5 cycles in not more than 9 min.

Depending on the reactivity of the acid and of the carbonate, the pendulum vacuum is switched off either after the 5th cycle or after the maximum specified time of 9 min depending on which of the two specified maxima is reached first.

Thereafter, 4.4 parts by weight of potassium bicarbonate, 3.0 parts by weight of magnesium oxide and 1.0 part by weight of citric acid are admixed and 0.55 part by weight of a citric acid solution in 50% ethanol is added to the mixture with stirring. The reaction takes place under a second, predetermined pendulum vacuum between 450 and 750 mbar with 2 cycles in 5 min at the most. After the 2nd cycle or after 5 min the pendulum vacuum is switched off and the product is dried under full vacuum with slow stirring. After sieving to the desired particle size, a flavor can be mixed with the granules obtained, and the granules can be either filled into sachets or pressed to give tablets.

Example 4

The method according to EP-B-0 076 340 (prior art) was compared with the method according to the invention.

a) Method According to EP-B-0 076 340 (Comparative Experiment)

Citric acid, ascorbic acid and sweeteners were heated to 50° C. in a vacuum granulator. Thereafter, sodium bicarbonate was admixed and evacuation to 10 mbar was effected. 21 ml of water were then added and the reaction was started. The pressure increased to 1 bar in 30 sec, and the granules became very plastic and adhered to the stirrer, with the result that the stirrer was virtually blocked.

The product was then dried by means of a vacuum to 20 mbar in 15 min. After a further addition of 21 ml of water, the reaction was started again and the pressure increased to 1 bar in 45 sec, and the granules became very plastic and spherical agglomerates some of them large, formed. Addition of sodium carbonate and subsequent drying were carried out, the product drying only slowly and it being possible to reach only 17 mbar in 25 min.

b) Method According to the Invention

Citric acid, ascorbic acid and sweeteners were heated to 50° C. in the same vacuum granulator. Thereafter, sodium bicarbonate was admixed and 21 ml of water were added. A pendulum vacuum was then switched on, fixed between a first vacuum value of 500 mbar and a second vacuum value of 900 mbar. 3 cycles were carried out in 65 sec. The material was slightly lumpy and only somewhat plastic and could be readily mixed by the stirrer without resulting in blockage or the formation of lumps. The addition of sodium carbonate and subsequent drying were then carried out, during which 15 mbar were reached in 17 min.

Result:

The method according to the invention is substantially shorter and the granulation takes place in a substantially more controlled and uniform manner (overreaction is prevented). According to the method of EP-B-0 076 340 an additional method step comprising drying, further addition of liquid and a further complete reaction procedure, are necessary in order to obtain a product equivalent to the method according to the invention, i.e. a stable product. As a result of the additional method step comprising a second granulation with drying, the method according to the prior art takes substantially longer and the critical granulation reaction has to be carried out a second time, a nonuniform structure of the granules resulting through the formation of spherical agglomerates, some of which are large.

Example 5

Increase of Carbon Dioxide Partial Pressure

This example was carried out according to example 4 b) but with an increase in the carbon dioxide partial pressure, as described below.

Citric acid, ascorbic acid, sweeteners and sodium bicarbonate were heated in a vacuum granulator with pendulum vacuum and with aspiration of carbon dioxide during the cycles until 50° C. were reached, evacuation being effected to 200 mbar in each cycle and then a pressure increase to 800 mbar being effected. After addition of 21 ml of water, a further 10 cycles were carried out with inflow of carbon dioxide. After addition of sodium carbonate, the granules were dried by means of a vacuum, a further 20 cycles being carried out with inflow of carbon dioxide during the final drying. On checking the stability to storage after one week, these granules showed values improved by 30% compared with the control sample produced according to example 4 b).

The invention claimed is:

1. A method for the production of effervescent granules, in which at least one acidic effervescent component and at least one $CO_2$-eliminating alkaline effervescent component are loaded as reactive constituents into an evacuatable container and react with one another in a vacuum with stirring, the container being evacuated to a first vacuum value after loading with the reactive constituents, whereupon—after reaction-related evolution of gas and pressure increase up to a second vacuum value—effervescent granules are formed, and wherein the reaction is carried out in a vacuum range of from 200 to 900 mbar; and wherein evacuation of the container to a first vacuum value within said vacuum range and reaction-related gas evolution and pressure increase to a second vacuum value within said vacuum range is repeated cyclically by repeated, controlled opening and closing of a valve to a vacuum pump; and wherein said reaction takes place without intermediate drying; and whereupon after a number of cycles the reaction is stopped by drying the resulting effervescent granules in a vacuum.

2. The method as claimed in claim 1, wherein a value in the range of from 200 to 700 mbar, is specified as the first vacuum value.

3. The method as claimed in claim 1, wherein a value of from 200 to 700 mbar, is specified as the pressure difference between the first and second vacuum value, and the second vacuum value is not more than 900 mbar.

4. The method as claimed in claim 1, wherein at least one of the first vacuum value and/or the second vacuum value are varied from cycle to cycle.

5. The method as claimed in claim 3, wherein the pressure difference is varied from cycle to cycle.

6. The method as claimed in claim 1, wherein at least one of a maximum number of cycles or a maximum duration of the reaction is established in advance for the reaction granulation, the reaction is stopped after one of the two maxima is reached.

7. The method as claimed in claim 6, wherein a number of cycles of from 2 to 100 is established.

8. The method as claimed in claim 6, wherein a cycle lasts for from 30 to 240 sec.

9. The method as claimed in claim 6, wherein a duration of the reaction of from 1 to 40 min, is established for the reaction granulation.

10. The method as claimed in claim 1, wherein the reaction granulation is carried out at a temperature of from 20 to 80° C.

11. The method as claimed in claim 1, wherein a granulating liquid, which is introduced, into the container before or during the first evacuation step, is added to at least one of the reactive effervescent constituents or the mixture of the reactive effervescent constituents.

12. The method as claimed in claim 1, wherein at least one reactive effervescent constituent is present as a hydrate.

13. The method as claimed in claim 1, wherein at least one of edible organic acids or salts thereof are used as acidic effervescent components, and at least one of carbonates, or bicarbonates or magnesium oxide are used as alkaline effervescent components.

14. The method as claimed in claim 1, wherein, after the drying step, the effervescent granules are mixed with at least one pharmaceutical active substance.

15. The method as claimed in claim 14, wherein the effervescent granules are mixed with at least one active substance from the group consisting of analgesics, antipyretics, antihistamines, antiallergic agents, antibiotics, antidiabetic agents, oncolytic agents, expectorants, electrolytes, laxatives, vitamins, phytopharmaceuticals, cardiovascular agents, antidiarrhoeal agents, diuretics and agents which promote blood flow.

16. The method as claimed in claim 1, wherein carbon dioxide is passed in during the reaction cycles.

17. The method as claimed in claim 1, wherein, after drying is complete, carbon dioxide is aspirated into the container and the effervescent granules are treated with carbon dioxide.

18. The method of claim 1 which further comprises treating said effervescent granules with carbon dioxide in the course of their production or thereafter.

19. The method as claimed in claim 18, wherein said treating of the effervescent particles is effected in a closed container in a carbon dioxide-enriched atmosphere.

20. An effervescent particle, made according to the method of claim 1.

21. The effervescent particle as claimed in claim 20, which has a residual moisture content of from 0.01 to 1% by weight.

22. The effervescent particle in a form enriched with gaseous carbon dioxide, obtained in a method as claimed in claim 16.

23. The method of claim 1 wherein the reactive constituents loaded into said evacuatable container further comprise a granulating liquid.

24. The method of claim 2 wherein the first vacuum value is in a range of from 300 to 600 mbar.

25. The method of claim 3 wherein said pressure difference is from 300 to 500 mbar.

26. The method of claim 9 wherein the duration of the reaction is from 1 to 15 min.

27. The method of claim 10 wherein the reaction granulation is carried out at a temperature of from 40 to 60° C.

28. The method of claim 11 wherein granulating liquid is aspirated into the container.

29. The method of claim 14 wherein the effervescent granules are further mixed with at least one of excipients, neutral substances, sweeteners or flavors.

30. The method of claim 17 wherein said granules are treated with carbon dioxide with stirring.

31. The method of claim 19 wherein the treatment of the effervescent particles is effected with stirring.

32. The particle of claim 21 having a residual moisture content of from 0.1 to 0.8% by weight.

33. A reaction method for producing effervescent granules, which comprises
  a) loading at least one acidic effervescent component and at least one $CO_2$-eliminating alkaline effervescent component into an evacuatable container,
  b) evacuating said container to a first vacuum value in said container,
  c) reacting said acidic and said $CO_2$-eliminating alkaline effervescent components with one another in said vacuum with stirring to produce evolution of gas and a pressure increase up to a second vacuum value, and
  d) repeating b) and c) cyclically without drying to form effervescent granules, and
  e) stopping the reaction by drying said effervescent granules in a vacuum, wherein the reaction is carried out in a vacuum range of from 200 to 900 mbar.

34. The method of claim 33 wherein said first vacuum value is in the range of from 200 to 700 mbar.

35. The method of claim 33 wherein said second vacuum value is not more than 900 mbar and the pressure difference between said first vacuum value and said second vacuum value is from 200 to 700 mbar.

36. The method of claim 33 wherein at least one of said first vacuum value and said second vacuum value are varied from cycle to cycle.

37. The method of claim 35 wherein the pressure difference is varied from cycle to cycle.

38. The method of claim 33, which further comprises establishing in advance at least one of (1) a maximum number of cycles of repeating b) and c) or (2) a maximum duration of the reaction, and stopping the reaction after one of the two maxima is reached.

39. The method of claim 38 wherein said maximum number of cycles is from 2 to 100.

40. The method of claim 38 wherein a cycle lasts for from 30 to 240 seconds.

41. The method of claim 38 wherein said maximum duration of the reaction is from 1 to 40 minutes.

42. The method of claim 33 wherein said reaction is carried out at a temperature of from 20 to 80° C.

43. The method of claim 33, which further comprises adding a granulating liquid to at least one of the acidic effervescent component, the $CO_2$-eliminating alkaline effervescent component, or to their mixture before or during the first evacuation step.

44. The method of claim 33 wherein at least one of the acidic effervescent component or the $CO_2$-eliminating alkaline effervescent component is a hydrate.

45. The method of claim 33, wherein said acidic effervescent component is an edible organic acid or a salt thereof and wherein said $CO_2$-eliminating alkaline effervescent component is a carbonate, a bicarbonate or a magnesium oxide.

46. The method of claim 33, which further comprises
  f) after the drying step, mixing said effervescent granules with at least one pharmaceutical active substance.

47. The method of claim 46, wherein said at least one pharmaceutical active substance comprises an active substance selected from the group consisting of an analgesic, an antipyretic, an antihistamine, an antiallergic agent, an antibiotic, an antidiabetic agent, an oncolytic agent, an expectorant, electrolytes, a laxative, a vitamin, a phytopharmaceutical, a cardiovascular agent, an antidiarrhoeal agent, a diuretic and an agent that promotes blood flow.

48. The method of claim 33, which further comprises passing carbon dioxide into said container during c)-d).

49. The method of claim 33, which further comprises
  f) after drying is complete, aspirating carbon dioxide into the container to treat the effervescent granules with carbon dioxide.

50. The method of claim 33, which further comprises loading a granulating liquid into said evacuatable container prior to b).

51. The method of claim 33 wherein d) is repeated several times.

52. The method of claim 34 wherein said first vacuum value is in the range of from 300 to 600 mbar.

53. The method of claim 34 wherein said pressure difference is from 300 to 500 mbar.

54. The method of claim 41 wherein said maximum duration of the reaction is from 1 to 15 minutes.

55. The method of claim 42 wherein said reaction is carried out at a temperature of from 40 to 60° C.

56. The method of claim 43 wherein said granulating liquid is aspirated into the container.

57. The method of claim 46, which further comprises mixing said effervescent granules with at least one substance selected from the group consisting of an excipient, a neutral substance, a sweetener and a flavor.

58. The method of claim 49, which further comprises stirring said granules during said treatment with carbon dioxide.

59. The method of claim 49, which further comprises stirring said effervescent particles during said exposure to carbon dioxide.

* * * * *